United States Patent [19]

Schmalfuss et al.

[11] Patent Number: 4,822,165
[45] Date of Patent: Apr. 18, 1989

[54] DEVICE FOR ILLUMINATING COMPONENTS OF TRANSPARENT MATERIAL IN TESTING FOR IRREGULARITIES

[75] Inventors: Harald Schmalfuss, Rodgau; Friedel Sinsel, Frankfurt am Main; Reinhold Bolz, Floersheim, all of Fed. Rep. of Germany

[73] Assignee: Battelle-Institut e.V., Frankfurt am Main, Fed. Rep. of Germany

[21] Appl. No.: 62,182

[22] Filed: Jun. 15, 1987

[30] Foreign Application Priority Data

Jun. 14, 1986 [DE] Fed. Rep. of Germany ....... 3620108

[51] Int. Cl.$^4$ ............................................. G01N 21/88
[52] U.S. Cl. ................................... 356/239; 356/124; 356/426; 250/572
[58] Field of Search ............... 356/124, 237, 239, 426; 250/563, 572

[56] References Cited

U.S. PATENT DOCUMENTS

| 3,892,494 | 7/1975 | Baker et al. | 356/237 |
| 3,947,127 | 3/1976 | Bennett et al. | 356/124 |
| 3,988,068 | 10/1976 | Sprague | 356/124 |
| 4,460,273 | 7/1984 | Koizumi et al. | 250/563 |

FOREIGN PATENT DOCUMENTS

| 2337597 | 2/1974 | Fed. Rep. of Germany. |
| 3011014 | 10/1980 | Fed. Rep. of Germany. |
| 3237511 | 4/1984 | Fed. Rep. of Germany. |
| 1242780 | 7/1986 | U.S.S.R. | 356/237 |

Primary Examiner—F. L. Evans
Attorney, Agent, or Firm—Spencer & Frank

[57] ABSTRACT

A device for illuminating components of transparent material by dot-scanning so that the components may be tested for surface irregularities and occlusions which comprises a component rotatably mounted so that the component may be rotated on its axis at a predetermined speed, a light source for generating a parallel light beam for illuminating the component, and a mechanism for periodically linearly deflecting the light beam at a frequency greater than the predetermined rotational speed of the component. The periodically linearly deflecting mechanism is disposed in the path of the light beam between the parallel light beam generating source and the component. The device also includes a focusing lens for focusing the light beam in a testing plane, where the focusing lens is disposed between the periodically linearly deflecting mechanism and the component at a location whereby the focal point of the focusing lens is at the edge of the periodically linearly deflecting mechanism. The device further includes an adjustable tilting mirror disposed between the focusing lens and the component for deflecting the light beam onto the component, whereby the dot-scanning light beam can then be detected by a testing device.

9 Claims, 2 Drawing Sheets

DEVICE FOR ILLUMINATING COMPONENTS OF TRANSPARENT MATERIAL IN TESTING FOR IRREGULARITIES

BACKGROUND OF THE INVENTION

1. Field of the Invention

The invention in question concerns a device for illuminating components of transparent material so that the components may be tested for surface irregularities and occlusions.

Components of transparent material, for example optical or opthalmic lenses, must be tested for flaws prior to their utilization, particularly for surface flaws such as scratches, smears, cracks, chipping, stains, etc., and for occlusions such as bubbles or streaks. Such flaws would limit the usability of a lens if these were to exceed the limit values stated in DIN 3140.

Conventionally, the testing of optical components is carried out by personnel in the form of visual inspection. Such a test must be performed to a large extent in a darkened room. It is expensive, not sufficiently objective and, due to the high degree of monotony of the testing procedure, not sufficiently reliable.

2. Discussion of the Prior Art

Efforts have, therefore, been made to develop methods and devices for automatic, objective testing of optical components. From DE-OS No. 32 37 511, the method is known of placing optical components to be tested in the optical beam path of a television camera and of displaying through the component a test pattern on the camera. The disturbances caused by flaws in the component, produce a video signal which deviates from the control signal not influenced by the component. The flaw is deduced on the basis of the deviation between the control and actual signal. A device acting on this principle is rather expensive and is not able to detect smaller flaws, for example, those resulting from scratches, smears or hair-line cracks.

In order to increase the sensitivity of the testing procedure, it is recommended in DE-OS No. 30 11 014 that the component to be tested be illuminated completely, a television image be produced, and the video signal be analyzed line for line. This method is also complicated, expensive and not sufficiently exact.

An even older recommendation for a test method is to be found in DE-OS No. 23 37 597. According to this, a light ray is focused on the surface of the component to be tested and is punctiformly moved over the surface, at the same time being kept in focus. The light penetrating the component is reflected backwards, passes through the component again, and then falls onto a detector. Deviations in the intensity of the receiver signal make it possible to deduce a flaw and also to localize this.

A device acting on this principle is very expensive. It only allows that surface of the work-piece to be tested onto which the scanner ray is focused. Illumination of the object to be tested is, in this case, achieved in that the test piece rotates on its axis and the impinging light ray is slowly radially deflected in such a way that it describes a spiral-type pattern on the test piece, whereby its state of focus must be continuously readjusted according to the curvature of the surface to be scanned.

SUMMARY OF THE INVENTION

It is the intention of the present invention to create a device for the illumination of components of transparent material when testing for surface irregularities and occlusions, which enables the component, independent of its shape, to be constantly illuminated and, thus, a diffusion of light to be created over the entire volume of the component, making it possible to evaluate disturbance signals from any chosen plane of thickness whatever, in particular, from both surfaces of the component. The actual evaluation is carried out by means of a post-installed measuring system, which can be designed in various ways, for instance, according to the recommendation of the German Patent Application No. P 3620146.4 of the Applicant, with the title "Device for Testing Components of Transparent Material for Surface Irregularities and Occlusions", filed June 14th, 1986, which application corresponds to U.S. Application Ser. No. 062,181 filed June 15th, 1987.

This assignment is solved by a device, for illuminating components of transparent material by dot-scanning so that the the components may be tested for surface irregularities and occlusions which comprises a component rotatably mounted so that the component may be rotated on its axis at a predetermined speed, a light source for generating a parallel light beam for illuminating the component, and a mechanism for periodically linearly deflecting the light beam at a frequency greater than the predetermined rotational speed of the component. The periodically linearly deflecting mechanism is disposed in the path of the light beam between the parallel light beam generating source and the component. The device also includes a focusing lens for focusing the light beam in a testing plane, where the focusing lens is disposed between the periodically linearly deflecting mechanism and the component at a location whereby the focal point of the focusing lens is at the edge of the periodically linearly deflecting mechanism. The device further includes an adjustable tilting mirror disposed between the focusing lens and the component for deflecting the light beam onto the component, whereby the dot-scanning light beam can then be detected by a testing device.

With the device in accordance with the invention, a light beam is produced by the light source, which can be focused with a high degree of depth definition. A focusing lens, preferably designed as an f-theta lens, is used to focus the light beam. A focal point of this lens is in the center of rotation of the scanner, so that the rotation of the light beam deflected by the scanner is converted behind the lens into a parallel displacement. In this way, the component to be tested is illuminated by a light beam which displaces itself parallel along a diameter of the rotating component and, thus, produces an optical pattern. This spoke-shaped optical pattern, when the component is turned by 360, moves through the component once and, in this way, uniformly illuminates each point of the volume with light of approximately the same state of focus.

The radiation, the normal diffusion of which is disturbed by any possible flaws in the surfaces or inside the component, is detected in the post-installed testing system.

If, for instance, in respect of the components to be tested, lenses with extremely curved surfaces are concerned, it is possible that the optical pattern, in cases where the parts of the illumination system are in a position designed for less curved lenses, no longer detects those lens surfaces. For this reason, an adjustable tilting mirror is arranged between the focusing lens and the component to be tested. By means of this mirror, it is possible to adjust the illumination system to suit all factors of the component to be tested, i.e. to select the angle of impingement and the point of impingement of the scanning light beam in such a way that both surfaces and, thus, the entire volume of the component, are illuminated.

BRIEF DESCRIPTION OF THE DRAWINGS

On the basis of FIGS. 1 to 4 of the enclosed drawings, the invention is described more closely to the following. In detail.

DESCRIPTION OF THE PREFERRED EMBODIMENT

Figure 1:
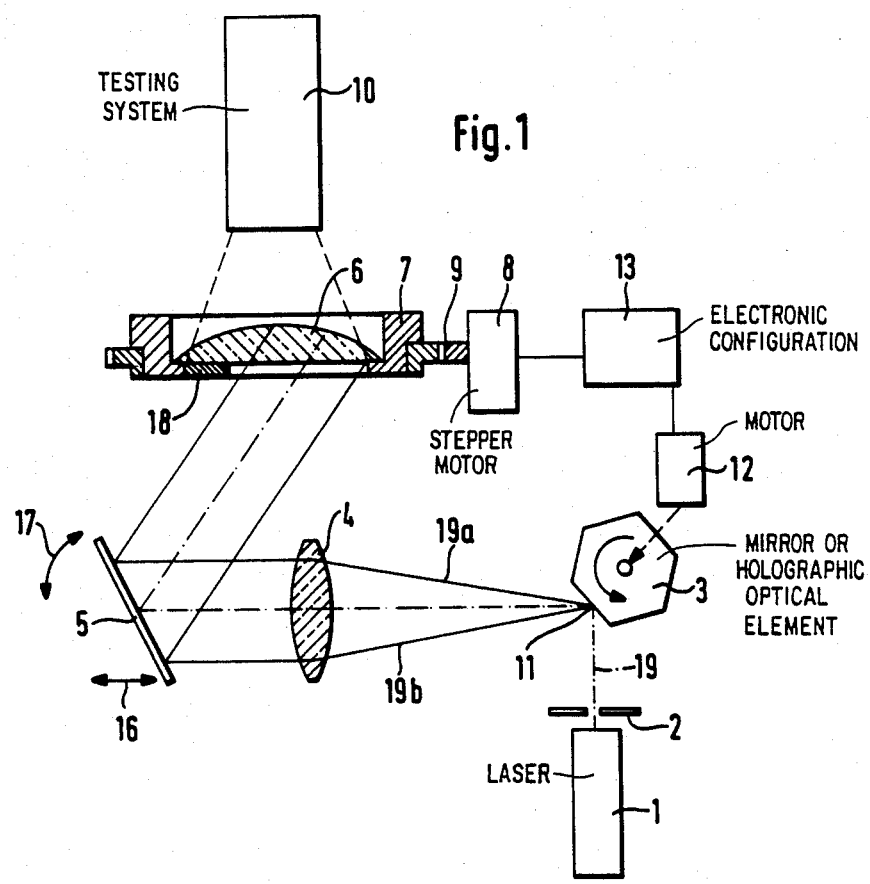
FIG. 1 is a diagrammatic illustration of one embodiment for the illumination system according to the invention.

In FIG. 1, a laser (1) which, for is preferably designed as a He-Ne laser and functions at an operational wavelength of 628 nm. A mode filter (2) is arranged in front of this laser. The parallel light beam (19) penetrating this filter, impinges at a point (11) on a polygonal mirror (3), which is revolved in the direction of the arrow by means of a motor (12). In this way, the light beam (19) between the extreme positions marked (19a) and (19b) is periodically deflected. The light beam (19) reflected by the mirror (3) penetrates a focusing lens (4), which, for reasons of advantage, is designed as an f-theta lens. The focal point of this lens coincides with the point of rotation (11) on the surface of the deflecting polygonal mirror (3). The deflected light beams (19a) and (19b) run parallel to each other behind the lens (4). These are deflected by means of a deflection mirror (5) onto the lens to be tested (6). The deflection mirror (5) can be moved mechanically in the direction of the arrow (16) and can be turned in the direction of the arrow (17).

The lens (6) to be tested is placed on a rotary plate (7), turned via a toothed wheel (9) by a stepper motor (8) and the motor (12) for turning the polygonal mirror (3) are synchronized via an electronic configuration (13).

In a known manner, it is also possible to have the scanner be a holographic optical element instead of a mirror.

Figure 2:
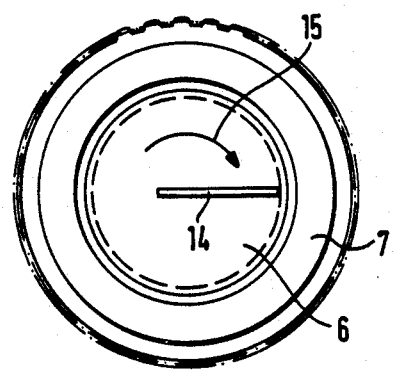
FIG. 2 is a horiziontal projection of the component to be tested shown in FIG. 1.

As shown in FIG. 2, by means of the illumination system there depicted, the lens (6) is illuminated in the form of a narrow optical pattern (14) which is penetrated by the light beam (19) between its extreme positions (19a) and (19b). Simultaneously, the lens (6) is turned in the direction of the arrow (15) by means of the stepper motor (8), so that, after one full revolution of the lens (6), the spoke-shaped optical pattern (14) has completely passed through the lens, i.e. during a complete revolution by 360, all volume elements of the lens (6) are illuminated. Illumination is by means of the deflected light beam (19), which has approximately the same state of focus on both surfaces of the lens (6).

A diagrammatically illustrated testing system (10), arranged, as seen in the direction of light, behind the lens (6) to be tested, absorbs the light penetrating the lens (6) and, from an irregular influencing of the light, for instance throught one of the surfaces of the lens (6), detects and localizes existing flaws.

An adjustable slit diaphragm (18) is arranged, as seen in the direction of light, in front of the lens (6), which limits the spoke-formed optical pattern (14). The light beam (19) is deflected in such a way that, in the extreme position (19b) it will impinge on the supporting plate (7). The slit diaphragm (18) then prevents disturbing reflections.

Figure 3:
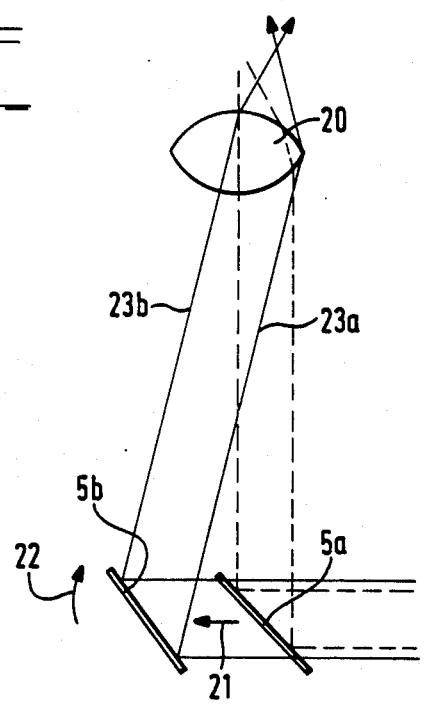
FIG. 3 illustrates the situation when illuminating a biconvex lens with extremely curved surfaces.

In FIG. 3, the lens to be tested is marked with (20). In this case, it is designed as a biconvex focusing lens with extremely curved surfaces. Due to this form of lens surface, when the reflexion mirror (5) is in a position (5a) for testing, for instance, the lens (6) in FIG. 1, light would not illuminate the entire volume of the lens (6). For this reason, the reflexion mirror (5) is moved in the direction of the arrow (21) and is turned in the direction of the arrow (22) and is then in position (5b). In this position, the light beam (19) generated by the laser (1) is deflected between the extreme positions (23a) and (23b). One sees that this optical pattern now uniformly covers both surfaces of the lens (20).

Figure 4:
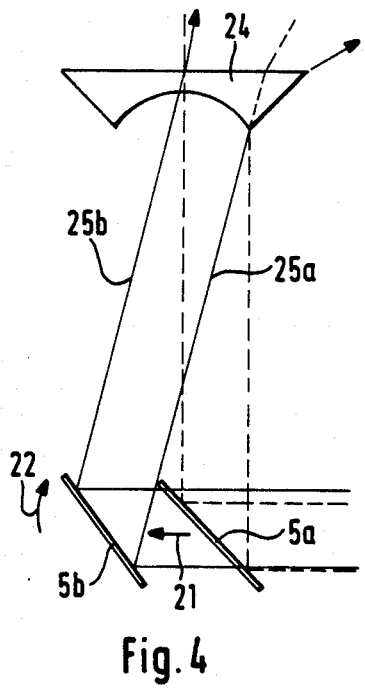
FIG. 4 illustrates the situation when illuminating a plano-concave lens with extremely curved concave surface.

The situation is similar when testing a lens (24) as shown in FIG. 4. The plano-concave lens illustrated there has an extremely curved concave surface and, with the deflection mirror (5) in normal position (5a), the entire lens volume would not be illuminated. For this reason, the mirror (5) is, also in this case, moved in the direction of the arrow (21) and turned in the direction of the arrow (22) until it is in position (5b). In this position, the light beam (19) is deflected between the extreme positions (25a) and (25b). One sees that now the entire volume of the lens (24) is uniformly illuminated.

SUMMARY

Device for Illuminating Components of Transparent Material in Testing for Irregularities (FIG. 1)

When testing components of transparent material for surface irregularities and occlusions, a device is used for illumination, whereby the component to be tested is so arranged as to be rotatable on its axis and is dot-scanned by means of a moving light ray.

To generate the scanning light ray, a light source, preferably a laser, which generates a parallel light beam, and a scanner which periodically linearly deflects this light beam at a high frequency in comparison to the speed of the component, are used. Behind the scanner, as seen in the direction of light, a focusing lens is provided, designed as an f-theta lens, the focal point of which is in the center of rotation of the scanner. By this means, the angular deflection of the light beam produced by the laser is converted by the scanner behind the focusing lens into a parallel displacement of the light beam between two extreme positions. Between the focusing lens and the component to be tested, an adjustable tilting mirror is provided to deflect the light beam onto the component. By means of this tilting mirror, the position of impingement and the angle of impingement of the scanning light beam can be selected in accordance with the requirements placed by the test piece.

We claim:
1. A device for illuminating components of transparent material by dot-scanning so that the the components may be tested for surface irregularities and occlusions, comprising:
   means for rotatably mounting the component so that the component may be rotated on its axis at a predetermined speed;

means for generating a parallel light beam for illuminating the component;

means for periodically linearly deflecting the light beam at a frequency greater than said predetermined rotational speed of the component, said periodically linearly deflecting means being disposed in the path of the light beam between said parallel light beam generating means and the component;

a focusing lens for focusing the light beam in a testing plane, said focusing lens being disposed between said periodically linearly deflecting means and the component at a location so that the focal point of said focusing lens is at the surface of said periodically linearly deflecting means, said focusing lens having a diameter which is larger than the extreme positions of said light beam produced when deflected by said periodically linearly deflecting means; and an adjustable tilting mirror disposed between said focusing lens and the component for deflecting the light beam onto the component, whereby the dot-scanning light beam can then be detected by a testing device.

2. A device as defined in claim 1, wherein said parallel light beam generating means is a laser.

3. A device as defined in claim 2, further comprising a mode filter disposed in the path of said light beam and adjacent said laser.

4. A device as defined in claim 1, wherein said periodically linearly deflecting means is a mirror.

5. A device as defined in claim 4, wherein said mirror is a rotating polygonal mirror.

6. A device as defined in claim 1, wherein said periodically linearly deflecting means is a holographic optical element.

7. A device as defined in claim 1, wherein said focusing lens has an optical axis; and said tilting mirror is movable in the direction of said optical axis of said focusing lens and is rotatable around an axis transverse to said optical axis.

8. A device as defined in claim 1, further comprising an adjustable slit diaphragm disposed in a portion of said light beam and adjacent to the component to be tested.

9. A device as defined in claim 1, wherein said means for rotatably mounting the component includes a stepper motor; and said device further comprises an electronic circuit means for synchronizing said stepper motor with said periodically linearly deflecting means.

* * * * *